US007523577B2

(12) United States Patent
Majerowski (10) Patent No.: US 7,523,577 B2
(45) Date of Patent: Apr. 28, 2009

(54) AIR FRESHENER WITH HOLDER

(75) Inventor: Amelia H. Majerowski, Kenosha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 388 days.

(21) Appl. No.: 11/396,755

(22) Filed: Apr. 3, 2006

(65) Prior Publication Data
US 2007/0251131 A1    Nov. 1, 2007

(51) Int. Cl.
*A47G 1/06* (2006.01)
(52) U.S. Cl. ........................... 40/768; 40/725; 422/124; 239/34
(58) Field of Classification Search ............... 206/45.24, 206/461, 462, 764; 239/34, 60; 40/745, 40/748, 750, 786, 789, 788
See application file for complete search history.

(56) References Cited

U.S. PATENT DOCUMENTS

| 882,710 A | 3/1908 | Pearsall |
|---|---|---|
| 886,840 A | 5/1908 | Mueller |
| 1,068,621 A | 7/1913 | Abraham |
| 1,204,934 A | 11/1916 | Burford et al. |
| 1,261,133 A | 4/1918 | Kidd |
| 1,802,999 A | 4/1931 | Budd |
| 1,940,328 A | 12/1933 | Schrotenboer |
| 2,268,529 A | 12/1941 | Stiles |
| 2,469,656 A | 5/1949 | Lienert |
| 2,550,954 A | 5/1951 | Benedict |
| 2,577,320 A | 12/1951 | Fenyo |
| 2,579,715 A | 12/1951 | Wilson et al. |
| D169,871 S | 6/1953 | Speer et al. |
| 2,779,624 A | 1/1957 | Friedman |
| 2,840,689 A | 6/1958 | Kazor |
| 3,178,844 A | 4/1965 | Christian |
| 3,424,380 A | 1/1969 | Curran |
| 3,540,146 A | 11/1970 | Watkins |
| 3,544,007 A | 12/1970 | Bordman |
| 3,558,055 A | 1/1971 | Storchheim |
| 3,570,160 A | 3/1971 | Spertus |
| 3,741,711 A | 6/1973 | Bryant |
| 3,790,081 A | 2/1974 | Thornton et al. |
| 3,804,330 A | 4/1974 | Miller, Jr. et al. |

(Continued)

FOREIGN PATENT DOCUMENTS

EP    1082970 A1    3/2001

(Continued)

OTHER PUBLICATIONS http://www.glade.com/piso.asp.

(Continued)

*Primary Examiner*—Paul N Dickson
*Assistant Examiner*—Shin Kim (57) ABSTRACT

A device that is adapted to discharge a volatile material includes a display frame with a front face and a rear face. An opening is disposed in the front face. A dispenser is disposed within the display frame. The dispenser comprises a blister holding a volatile material and a permeable membrane extends across an open end of the blister. The rear face includes an integral foot member actuable between first and second states. The permeable membrane is disposed adjacent the front face and prevents the release of the volatile material in a first condition and permits the release of the volatile material through the opening in a second condition.

19 Claims, 8 Drawing Sheets

U.S. PATENT DOCUMENTS

| | | |
|---|---|---|
| 3,822,495 A | 7/1974 | Ohfuji |
| 3,948,445 A | 4/1976 | Andeweg |
| D243,402 S | 2/1977 | Irving |
| 4,009,384 A | 2/1977 | Holland |
| 4,055,672 A | 10/1977 | Hirsch |
| D247,573 S | 3/1978 | Schimanski |
| 4,101,720 A | 7/1978 | Taylor et al. |
| 4,157,787 A | 6/1979 | Schwartz |
| 4,158,440 A | 6/1979 | Sullivan et al. |
| 4,161,283 A * | 7/1979 | Hyman ................ 239/55 |
| 4,165,573 A | 8/1979 | Richards |
| 4,170,080 A | 10/1979 | Bergh et al. |
| 4,173,604 A | 11/1979 | Dimacopoulos |
| 4,184,099 A | 1/1980 | Lindauer et al. |
| 4,254,910 A | 3/1981 | Martin |
| 4,285,468 A | 8/1981 | Hyman |
| D260,503 S | 9/1981 | Stangarone |
| 4,293,095 A | 10/1981 | Hamilton et al. |
| 4,314,915 A | 2/1982 | Wiegers et al. |
| D263,334 S | 3/1982 | Schimanski |
| 4,327,056 A | 4/1982 | Gaiser |
| D269,838 S | 7/1983 | Altonga |
| 4,411,829 A | 10/1983 | Schulte-Elte et al. |
| D271,359 S | 11/1983 | Le |
| 4,434,306 A | 2/1984 | Kobayashi et al. |
| D275,223 S | 8/1984 | Marxen |
| D275,700 S | 9/1984 | Marxen |
| 4,476,171 A | 10/1984 | Takeuchi |
| 4,493,011 A | 1/1985 | Spector |
| D279,146 S | 6/1985 | McCaffrey |
| D280,363 S | 9/1985 | Wisecup, Jr. |
| 4,549,250 A | 10/1985 | Spector |
| 4,580,581 A | 4/1986 | Reece et al. |
| D288,003 S | 1/1987 | Hoyt |
| 4,634,614 A | 1/1987 | Holzner |
| 4,695,435 A | 9/1987 | Spector |
| 4,714,984 A | 12/1987 | Spector |
| 4,720,409 A | 1/1988 | Spector |
| D296,957 S | 8/1988 | Gordon et al. |
| 4,762,275 A | 8/1988 | Herbert et al. |
| 4,781,895 A | 11/1988 | Spector |
| 4,794,714 A | 1/1989 | Weisgerber |
| 4,809,912 A | 3/1989 | Santini |
| 4,814,212 A | 3/1989 | Spector |
| 4,849,606 A | 7/1989 | Martens, III et al. |
| 4,874,129 A | 10/1989 | DiSapio et al. |
| 4,883,692 A | 11/1989 | Spector |
| D305,703 S | 1/1990 | Wang |
| 4,898,328 A | 2/1990 | Fox et al. |
| 4,913,349 A | 4/1990 | Locko |
| 4,917,301 A | 4/1990 | Munteanu |
| 4,921,636 A | 5/1990 | Traas |
| 4,939,858 A | 7/1990 | Dailey |
| 4,959,087 A | 9/1990 | Kappernaros |
| 4,993,177 A | 2/1991 | Hudson |
| 4,995,555 A | 2/1991 | Woodruff |
| D320,266 S | 9/1991 | Kunze |
| 5,060,858 A | 10/1991 | Santini |
| D325,077 S | 3/1992 | Kearnes |
| 5,148,983 A | 9/1992 | Muniz |
| 5,148,984 A | 9/1992 | Bryson et al. |
| 5,163,616 A | 11/1992 | Bernarducci et al. |
| 5,170,886 A | 12/1992 | Holzner |
| 5,219,121 A | 6/1993 | Fox et al. |
| 5,230,867 A | 7/1993 | Kunze et al. |
| D339,238 S | 9/1993 | Hamilton |
| D339,242 S | 9/1993 | Sontag et al. |
| 5,247,745 A | 9/1993 | Valentino |
| 5,259,555 A | 11/1993 | Kiefer |
| 5,297,732 A | 3/1994 | Hahn |
| D346,068 S | 4/1994 | White |
| 5,304,358 A | 4/1994 | Hoyt et al. |
| 5,334,361 A | 8/1994 | Rafaelides et al. |
| 5,361,522 A | 11/1994 | Green |
| 5,367,802 A | 11/1994 | Rosenberg |
| D354,627 S | 1/1995 | Rowan |
| 5,395,047 A | 3/1995 | Pendergrass |
| 5,402,517 A | 3/1995 | Gillett et al. |
| D358,037 S | 5/1995 | Monroe |
| D360,461 S | 7/1995 | Gillespie |
| 5,439,100 A | 8/1995 | Gordon et al. |
| D361,896 S | 9/1995 | Bramley et al. |
| 5,462,006 A | 10/1995 | Thiruppathi |
| 5,478,505 A | 12/1995 | McElfresh |
| D366,107 S | 1/1996 | Shaffer |
| 5,503,332 A | 4/1996 | Glenn |
| D369,473 S | 5/1996 | Gluck |
| 5,529,243 A | 6/1996 | Hoyt et al. |
| D372,797 S | 8/1996 | Ilaria et al. |
| 5,556,192 A | 9/1996 | Wang |
| D374,777 S | 10/1996 | Agam |
| D376,002 S | 11/1996 | Upson |
| D376,420 S | 12/1996 | Rymer |
| D376,914 S | 12/1996 | Waszkiewicz |
| D380,822 S | 7/1997 | Decker et al. |
| 5,647,052 A | 7/1997 | Patel et al. |
| 5,651,942 A | 7/1997 | Christensen |
| D383,613 S | 9/1997 | Handler |
| D384,821 S | 10/1997 | Sugar |
| 5,679,334 A | 10/1997 | Semoff et al. |
| 5,711,955 A | 1/1998 | Karg |
| 5,716,000 A | 2/1998 | Fox |
| D392,031 S | 3/1998 | Miller |
| D392,032 S | 3/1998 | Zaragoza et al. |
| 5,735,460 A | 4/1998 | Eisenbraun |
| 5,744,106 A | 4/1998 | Eagle |
| 5,749,519 A | 5/1998 | Miller |
| 5,749,520 A | 5/1998 | Martin et al. |
| 5,782,409 A | 7/1998 | Paul |
| 5,788,155 A | 8/1998 | Martin et al. |
| 5,804,264 A | 9/1998 | Bowen |
| D399,298 S | 10/1998 | Whitehead |
| D401,767 S | 12/1998 | Leung |
| 5,845,847 A | 12/1998 | Martin et al. |
| D405,473 S | 2/1999 | Tikhonski et al. |
| D405,961 S | 2/1999 | Stangl |
| 5,875,968 A | 3/1999 | Miller et al. |
| 5,885,701 A | 3/1999 | Berman et al. |
| D407,809 S | 4/1999 | Hammond |
| 5,899,382 A | 5/1999 | Hayes et al. |
| 5,950,922 A | 9/1999 | Flinn |
| 5,961,043 A | 10/1999 | Samuelson et al. |
| 5,975,427 A | 11/1999 | Harries |
| 6,031,967 A | 2/2000 | Flashinski et al. |
| D424,812 S | 5/2000 | Kacius |
| 6,065,687 A | 5/2000 | Suzuki et al. |
| 6,106,786 A | 8/2000 | Akahoshi |
| 6,109,537 A | 8/2000 | Heath |
| D431,075 S | 9/2000 | Barraclough |
| 6,112,496 A | 9/2000 | Hugus et al. |
| 6,144,801 A | 11/2000 | Lehoux et al. |
| 6,152,379 A | 11/2000 | Sorgenfrey |
| 6,154,607 A | 11/2000 | Flashinski et al. |
| D435,100 S | 12/2000 | Pesu et al. |
| D437,404 S | 2/2001 | Wu |
| D439,964 S | 4/2001 | Wu |
| D441,441 S | 5/2001 | Upson |
| D445,262 S | 7/2001 | Rowan |
| 6,254,248 B1 | 7/2001 | McAuley et al. |
| 6,254,836 B1 | 7/2001 | Fry |
| D451,990 S | 12/2001 | Millet |
| 6,328,935 B1 | 12/2001 | Buccellato |
| D453,561 S | 2/2002 | Nelson |
| 6,354,710 B1 | 3/2002 | Nacouzi |

| | | | | | | |
|---|---|---|---|---|---|---|
| 6,358,577 | B1 | 3/2002 | Bowen et al. | EP | 1295613 A | 3/2003 |
| 6,363,734 | B1 | 4/2002 | Aoyagi | EP | 1 346 734 | 9/2003 |
| 6,367,706 | B1 | 4/2002 | Putz | GB | 2158356 A | 11/1985 |
| D456,620 | S | 5/2002 | Vincent | GB | 2 254 558 | 10/1992 |
| D456,888 | S | 5/2002 | Buthier | GB | 3003643 | 11/2002 |
| D461,006 | S | 7/2002 | Buthier | GB | 3003644 | 6/2003 |
| D461,393 | S | 8/2002 | Aubert | GB | 3005817 | 7/2003 |
| 6,435,423 | B2 | 8/2002 | Hurry et al. | GB | 3007046 | 9/2003 |
| 6,478,440 | B1 | 11/2002 | Jaworski et al. | GB | 3007049 | 9/2003 |
| 6,484,425 | B1 | 11/2002 | Hirsch | GB | 3007052 | 9/2003 |
| 6,526,636 | B2 | 3/2003 | Bernhardt | GB | 3007053 | 9/2003 |
| 6,548,015 | B1 | 4/2003 | Stubbs et al. | GB | 3007054 | 9/2003 |
| 6,555,068 | B2 | 4/2003 | Smith | GB | 3007055 | 9/2003 |
| D476,726 | S | 7/2003 | Rosenberg | GB | 3007056 | 9/2003 |
| 6,610,254 | B1 | 8/2003 | Furner et al. | GB | 3007057 | 9/2003 |
| D479,742 | S | 9/2003 | Hollingsworth | GB | 3007233 | 9/2003 |
| 6,618,974 | B2 | 9/2003 | Szalay | GB | 3007045 | 10/2003 |
| 6,627,857 | B1 | 9/2003 | Tanner et al. | GB | 3012024 | 2/2004 |
| D480,221 | S | 10/2003 | Luciano | GB | 3012025 | 2/2004 |
| D481,113 | S | 10/2003 | Groene et al. | GB | 3012026 | 2/2004 |
| 6,631,852 | B1 | 10/2003 | O'Leary | GB | 3007048 | 10/2005 |
| 6,638,591 | B2 | 10/2003 | Bowen et al. | JP | HA05015803 | 8/1993 |
| D481,785 | S | 11/2003 | Koike | JP | 08-241039 | 9/1996 |
| 6,643,967 | B1 | 11/2003 | Bloom | JP | 9-84863 | 3/1997 |
| 6,648,239 | B1 | 11/2003 | Myny et al. | JP | D1027932 | 9/1998 |
| 6,663,838 | B1 | 12/2003 | Soller et al. | JP | 10-263068 | 10/1998 |
| D485,607 | S | 1/2004 | Wu | JP | D1195937 | 2/2004 |
| 6,691,870 | B1 * | 2/2004 | Palm et al. ............. 206/462 | NL | 000194709-0001 | 9/2004 |
| D487,308 | S | 3/2004 | Engerant | NL | 000205661-0001 | 10/2004 |
| 6,705,541 | B2 * | 3/2004 | Schuehrer et al. ........ 239/34 | NL | 000252358-0001 | 2/2005 |
| 6,714,725 | B2 | 3/2004 | Grone et al. | NL | 000252366-0001 | 2/2005 |
| 6,722,578 | B2 | 4/2004 | Skalitzky et al. | WO | WO 96/33605 | 10/1996 |
| 6,730,311 | B2 | 5/2004 | Maleeny et al. | WO | WO97/22370 A | 6/1997 |
| 6,749,672 | B2 | 6/2004 | Lynn | WO | WO 00/23121 | 4/2000 |
| 6,790,436 | B2 | 9/2004 | Williams et al. | WO | WO 03/068276 | 8/2003 |
| 6,808,791 | B2 | 10/2004 | Curro et al. | WO | WO 2007/096432 | 8/2007 |
| D498,524 | S | 11/2004 | Morillas | | | |
| D498,525 | S | 11/2004 | Harbutt et al. | | | |
| D498,836 | S | 11/2004 | Morillas | | | |
| 6,826,863 | B1 | 12/2004 | Goodfellow | | | |
| 6,889,840 | B2 * | 5/2005 | Schein et al. ............. 206/704 | | | |
| 6,998,581 | B2 | 2/2006 | Currie | | | |
| 7,175,815 | B2 | 2/2007 | Yamasaki et al. | | | |
| 2003/0007887 | A1 | 1/2003 | Roumpos et al. | | | |
| 2003/0017129 | A1 | 1/2003 | Maleeny et al. | | | |
| 2003/0085297 | A1 | 5/2003 | Huang | | | |
| 2003/0089791 | A1 | 5/2003 | Chen et al. | | | |
| 2003/0094503 | A1 | 5/2003 | Rymer et al. | | | |
| 2003/0200690 | A1 | 10/2003 | Galloway | | | |
| 2004/0000596 | A1 | 1/2004 | Cuthbert | | | |
| 2004/0057975 | A1 | 3/2004 | Maleeny et al. | | | |
| 2004/0094636 | A1 | 5/2004 | Channer | | | |
| 2004/0135000 | A1 | 7/2004 | Buthier | | | |
| 2004/0262418 | A1 | 12/2004 | Smith et al. | | | |
| 2004/0262421 | A1 | 12/2004 | Hurry et al. | | | |
| 2005/0001337 | A1 | 1/2005 | Pankhurst | | | |
| 2005/0103880 | A1 | 5/2005 | Taite | | | |
| 2005/0145711 | A1 | 7/2005 | Blondeau et al. | | | |
| 2005/0196571 | A1 | 9/2005 | Penny et al. | | | |
| 2006/0000920 | A1 | 1/2006 | Leonard | | | |

FOREIGN PATENT DOCUMENTS

| | | |
|---|---|---|
| EP | 0 645 081 | 7/2001 |

OTHER PUBLICATIONS http://www.glade.com/plugins.asp.
http://www.airwick.us/product page/product.html.
http://www.racerwheel.com/tcr-cz-103.html.
http://www.racerwheel.com/tcr.cz.102a.html.
http://www.giftsandgadgetsonline.com/ioairfrwilif.html.
http://www.allproducts.com/gift/sundeal/02-ac105.html.
http://us.shop.com/cc.amos?main=catalog&pcd=783942&adtg=05180436&GA=1.
http://www.autobarn.net/skulrotairfr.html?AID=10274001&PID=613288.
http://www.negativeiongenerators.com/XJ-201ionicfreshener.html.
http://www.buylighting.com/Odor eliminating light bulbs.html.
Int'l Search Report and Written Opinion Appl. No. PCT/US2005/023226 dated Sep. 12, 2005.
Int'l Search Report and Written Opinion Appl. No. PCT/US2005/023228 dated Nov. 3, 2005.
International Search Report & Written Opinion for PCT/US2007/008116 dated Nov. 26, 2007.
International Search Report in PCT/US2007/001568 dated Jun. 29, 2007.
International Search Report and Written Opinion in PCT/US2007/008035 dated Aug. 2, 2007.

* cited by examiner

FIG. 18

AIR FRESHENER WITH HOLDER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present invention generally relates to a volatile material dispensing system, and more particularly, to a volatile material dispenser in combination with an adjustable chipboard holder.

2. Description of the Background

Volatile material dispensers have been used to provide fragrances to office or home settings. One such dispenser is an ornamental design for a combined picture frame and potpourri holder. The design includes front and rear panels angled from each other. A recess is centered within the front panel to provide an area to insert a photograph. A bridge connects both the front and rear panels.

Another such ornamental design for a dispenser includes a combined air freshener and picture frame. The frame includes front and rear faces, wherein the front face includes two rectangular stepped portions extending outwardly therefrom and the rear face is planar. An opening extends through the front and rear faces adjacent an upper portion of the frame.

Yet another dispenser includes first and second panels. A base joins the first and second panels to provide a platform to support the device in a tent configuration. The second side panel has a tab extending therefrom. Means are provided to capture the tab that is associated with the first side panel. An opening in one of the side panels is provided for mounting a volatile material filled reservoir.

SUMMARY OF THE INVENTION

According to one embodiment of the present invention, a device adapted to discharge a volatile material includes a display frame having a front face and a rear face. An opening is disposed in the front face. A dispenser is disposed within the display frame. The dispenser comprises a blister holding a volatile material and a permeable membrane extends across an open end of the blister. The rear face includes an integral foot member actuable between first and second states. The permeable membrane is disposed adjacent the front face and prevents the release of the volatile material in a first condition and permits the release of the volatile material through the opening in a second condition.

According to another embodiment of the present invention, a substantially flat blank adapted for assembly into a dispensing system includes a first wall portion with a removable cover extending across a first opening. A second wall portion is hingedly connected to a first end of the first wall portion about a first fold line. A third wall portion is hingedly connected to an end of the second wall portion about a second fold line. The third wall portion further includes a second opening. A fourth wall portion is hingedly connected to a second end of the first wall portion about a third fold line. The fourth wall portion further includes a third opening adapted to receive a reservoir of a volatile material holding dispenser. The second and third openings are substantially the same size and are adapted to align within one another during a first in use position.

According to yet another embodiment of the present invention, a method of operating a volatile material dispenser includes the step of providing an inverted V-shaped structure that has first and second sides. The first side retains a volatile material dispensing cartridge and the second side includes a support member actuable between first and second positions. A different step comprises activating the volatile material dispensing cartridge. Another step includes disposing the support member in at least one of the first and second positions. The first position is characterized by the support member being substantially flush with the first side and the second condition is characterized by the support member being angled from the first side a distance sufficient to support the V-shaped structure.

BRIEF DESCRIPTION OF THE DRAWINGS

Other aspects and advantages of the present invention will become apparent upon reading the following detailed description and upon reference to the drawings in which.

DETAILED DESCRIPTION OF THE INVENTION

Figure 1:
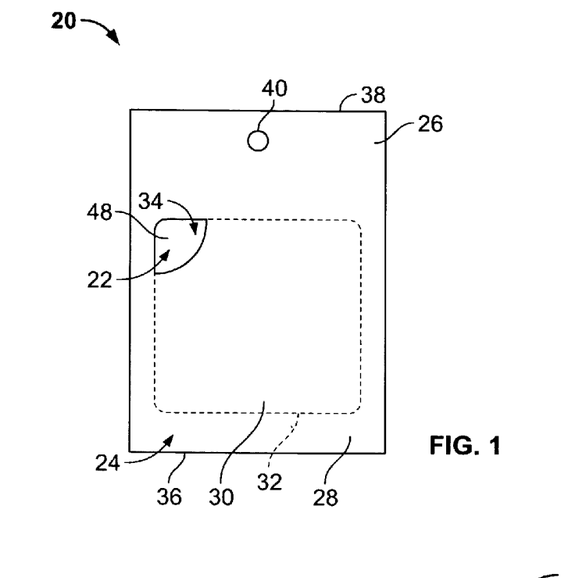
FIG. 1 is front elevational view of the dispensing system in a first state that includes a frame and a dispenser.

Referring to FIG. 1, a volatile material dispensing system 20 is illustrated. The dispensing system 20 includes a volatile material dispenser 22 and a display frame 24. The frame 24 is operable between first and second states to provide a user various manners of utilizing the present dispensing system 20.

FIG. 1 depicts the display frame 24 in the first state. A front face 26 of the display frame 24 comprises a first wall portion 28. The first wall portion 28 is substantially rectangular in shape and has a width of about 3.5 in. and a height of about 5 in. A cover 30 is provided within the front wall portion 28 and attached thereto by a perforated section 32 about a periphery of the cover 30. The cover 30 is substantially square except for an arcuately shaped portion that has been removed from an upper corner of the cover 30. The removed portion defines a slot 34. The cover 30 is substantially centered about the width of the front face 26 and is directed closer to a bottom end 36 of the display frame 24 than a top end 38 thereof. A hole 40 is disposed within the first wall portion 28 adjacent the top end 38.

Figures 2, 3:
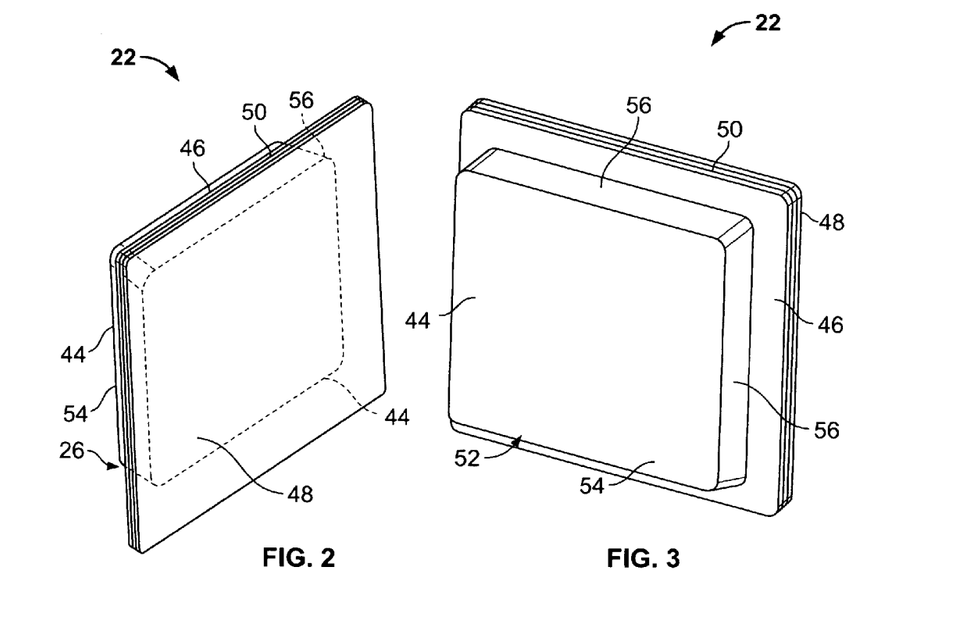
FIG. 2 is an front isometric view of the dispenser of FIG. 1.
FIG. 3 is a rear isometric view of the dispenser of FIG. 1.

The cover 30 overlies the dispenser 22 further illustrated in FIGS. 2-5. With reference to FIGS. 2 and 3, the dispenser 22 or cartridge comprises a blister 44, a peripheral flange 46, and an impermeable laminate 48 releasably adhered to the blister 44 and the flange 46. The blister 44 includes a non-porous permeable membrane 50 and a cup-shaped structure 52 or reservoir. The cup-shaped structure 52 includes a bottom wall 54 and four side walls 56 that in conjunction with the permeable membrane 50 act as a sealed reservoir to contain a volatile material 58. Illustratively, the cup-shaped structure 52 and the permeable membrane 50 are formed from clear and/or translucent materials, thereby allowing the volatile material 58 to be visible therethrough. The peripheral flange 46 is planar and is coupled to and extends outwardly from top edges of the cup-shaped structure 52. In one embodiment, the peripheral flange 46 extends outwardly from upper edges of the side walls 56 and is integrally formed therewith. The present dispenser 22 and the volatile material 58 are similar to those described in U.S. patent application Ser. No. 10/881,816, the disclosure of which is herein incorporated by reference in its entirety.

Figure 4:
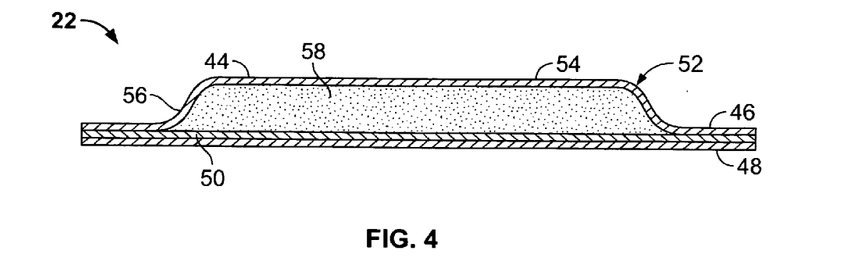
FIG. 4 is a cross-sectional view of the dispenser of FIG. 2 along the lines 4-4 in a first condition.

FIG. 4 illustrates the dispenser 22 in a first condition. The dispenser 22 is completely or substantially full in the first condition, i.e., little or no volatile material 58 has diffused through the permeable membrane 50 because the impermeable laminate 48 has not been removed from the blister 44. There is substantially no diffusion of the volatile material 58 when the dispenser 22 is filled and the impermeable laminate 48 covers the permeable membrane 50. Illustratively, the impermeable laminate 48 is removed from the blister 44 by a user grasping an end of the impermeable laminate 48 and peeling it off the blister 44. A tab 60, extension, or other means for grasping may be included as an extension of the impermeable laminate 48 to aid in removal of same. The extension may be at the corners, ends, and/or on the surface of the impermeable laminate 48.

Figure 5:
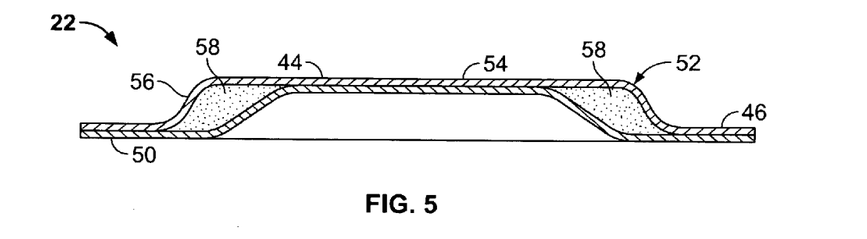
FIG. 5 is a cross-sectional view of the dispenser of FIG. 2 along the lines 5-5 in a second condition.

Following removal of the impermeable laminate 48, the dispenser 22 begins to transition from a full or first condition (FIG. 4) to an empty or second condition (FIG. 5). There may be a small amount of the volatile material 58 that remains in the blister 18 and the dispenser 22 will still be considered to have reached the second condition. As the volatile material 58 diffuses through the permeable membrane 50, the permeable membrane 50 slowly collapses upon the bottom wall 54. With reference to FIG. 5, following diffusion of the volatile material 58 across the permeable membrane 50 there is less volatile material 58 contained within the dispenser 22. Substantially no new air enters the dispenser 22 subsequent to diffusion of the volatile material 58. The result of this is a pressure gradient across the permeable membrane 50, with a higher pressure existing in the ambient air than the pressure in the dispenser 22. The pressure gradient causes the ambient air to exert a net positive pressure upon the dispenser 22, which presses the permeable membrane 50 against the remaining volatile material 58 and ultimately the bottom wall 54.

Figure 6:
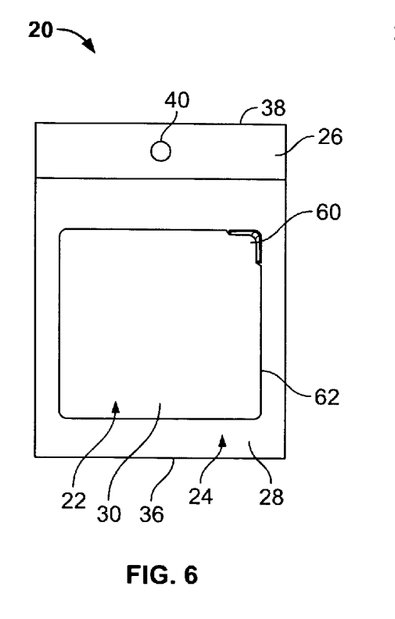
FIG. 6 is a front elevational view of the dispensing system of FIG. 1 with a front cover removed therefrom.

With reference again to FIG. 1, a portion of the impermeable laminate 48 is visible through the slot 34. The dispensing system 20 is activated by removing the cover 30 from the display frame 24, such as is depicted in FIG. 6. The cover 30 is removed by grabbing a portion of the cover 30 within the slot 34 and pulling the cover 30 outwardly away from the display frame 24. When a sufficient force is exerted upon the cover 30, same will tear away from the first wall portion 28 and provide a substantially square opening 62. The opening 62 in one embodiment has length and width measurements of about 2.876 in. The impermeable laminate 48 is viewable and accessible through the opening 62. The impermeable laminate 48 extends a distance substantially coterminous with a width and height of the opening 62. The impermeable laminate 48 is removed by grasping a portion of the laminate 48, such as the tab 60, and pulling the laminate 48 off of the blister 44. Removal of the impermeable laminate 48 allows the dispenser 22 to transition from the first condition (FIG. 4) to the second condition (FIG. 5), thereby allowing for the volatile material 58 to be dispersed into the atmosphere.

Figure 7:
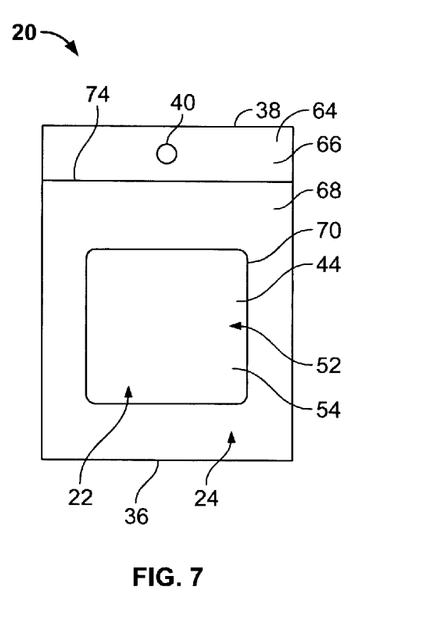
FIG. 7 is rear elevational view of the dispensing system of FIG. 1.
Figure 8:
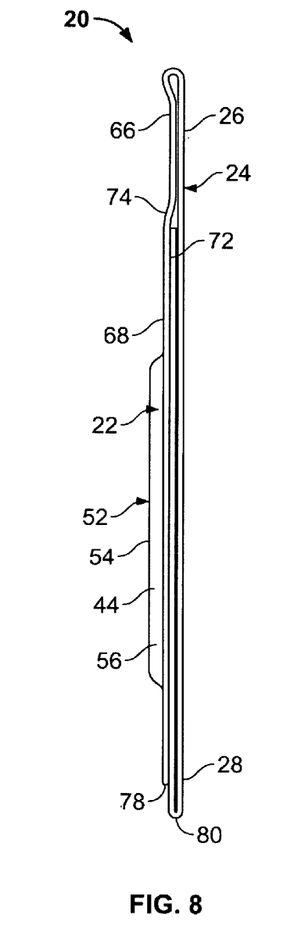
FIG. 8 is a side elevational view of the dispensing system of FIG. 1.
Figure 9:
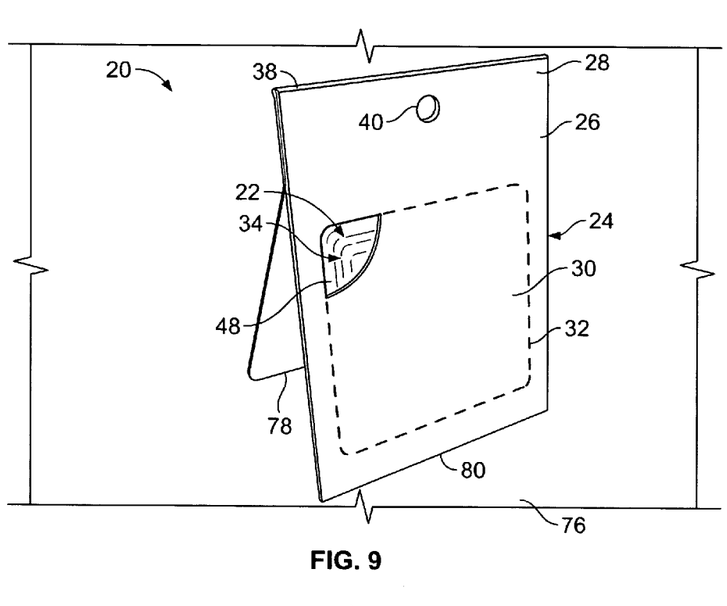
FIG. 9 is an front isometric view of the dispensing system of FIG. 1 in a second state.
Figure 10:
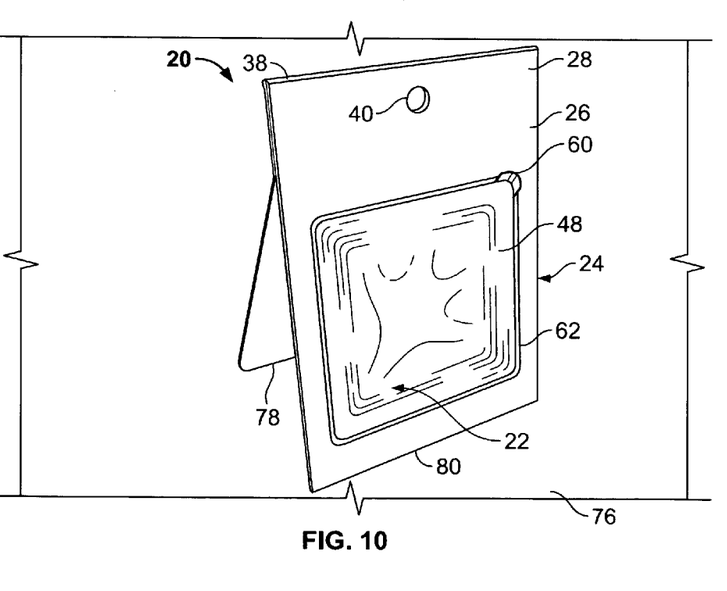
FIG. 10 is a front isometric view of the dispensing system of FIG. 9 with a front cover removed therefrom.

A rear face 64 of the display frame 24 is depicted in FIG. 7. The rear face 64 comprises second and third wall portions 66, 68, respectively. The second wall portion 66 is substantially rectangular in shape and has a width of about 3.5 in. and a height of about 1 in. The third wall portion 68 is integrally connected to the second wall portion 66 and has a width of about 3.5 in. and a height of about 4 in. A second opening 70 is provided within the third wall portion 66. The second opening 70 is substantially square-shaped and has length and width dimensions substantially equal to or greater than the length and width dimensions of the cup-shaped structure 52 of the blister 44. In one embodiment, the second opening 70 is dimensioned to be smaller than the opening 62 of the first wall portion 28 and has length and width measurements of about 2.313 in. The second opening 70 is centered about the width of the rear face 64 and is disposed closer to the bottom end 36 of the display frame 24 than the top end 38. The hole 40 extends through the second wall portion 66 adjacent the top end 38 of the display frame 24. The cup-shaped structure 52 protrudes through the second opening 70. In other embodiments, the cup-shaped structure 52 partially protrudes into the second opening 70 or is substantially aligned therewith. FIG. 8 provides a side elevational view that illustrates the extent to which the cup-shaped structure 52 extends through the second opening 70 in the present embodiment. The distance the cup-shaped structure 52 extends through the second opening 70 may be modified by adjusting the dimensions of the dispenser 22 and/or the display frame 24. For example, one or more of the first wall portion 28, the second wall portion 66, the third wall portion 68, or a fourth wall portion 72 may be manufactured from a material having a different thickness to adjust the degree to which the cup-shaped structure 52 extends though the second opening 70.

The dispensing system of FIGS. 1 and 6-11 depict the dispensing system 20 in the first state. The first state is characterized by a having the first, second, third, and fourth wall portions 28, 66, 68, 72 disposed in a substantially parallel manner to each other. Portions of the dispenser 22, such as the bottom wall 54 and the impermeable laminate 48, are also parallel to the first, second, third, and fourth wall portions 28, 66, 68, 72. Typically, a cord or other member is strung through the hole 40 and the dispensing system 20 is hung from a support structure (not shown). In a different embodiment, the dispensing system 20 is propped against a wall or other surface or may be laid upon a support surface. There are numerous manners of deploying the dispensing system 20 in the first state that users may employ.

Figure 11:
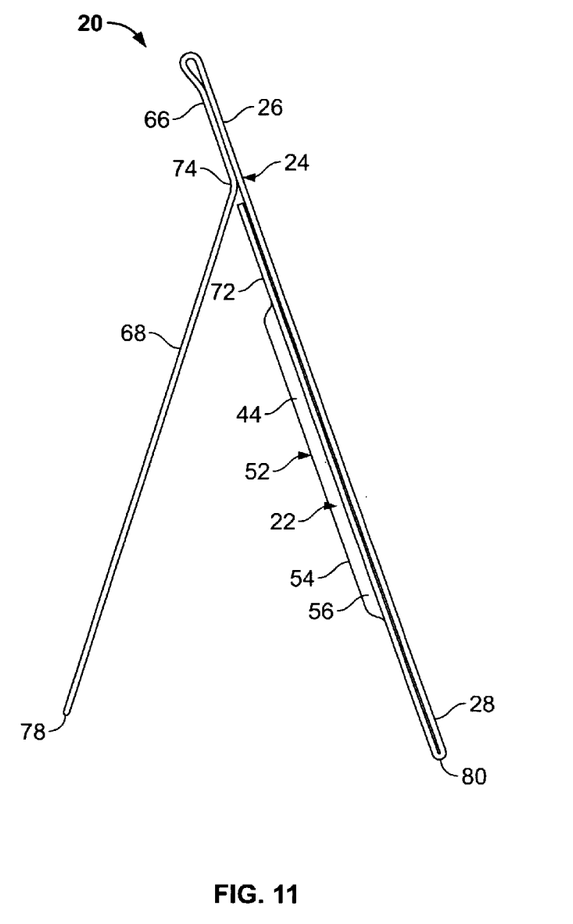
FIG. 11 is a side elevational view of the dispensing system of FIG. 9.
Figure 12:
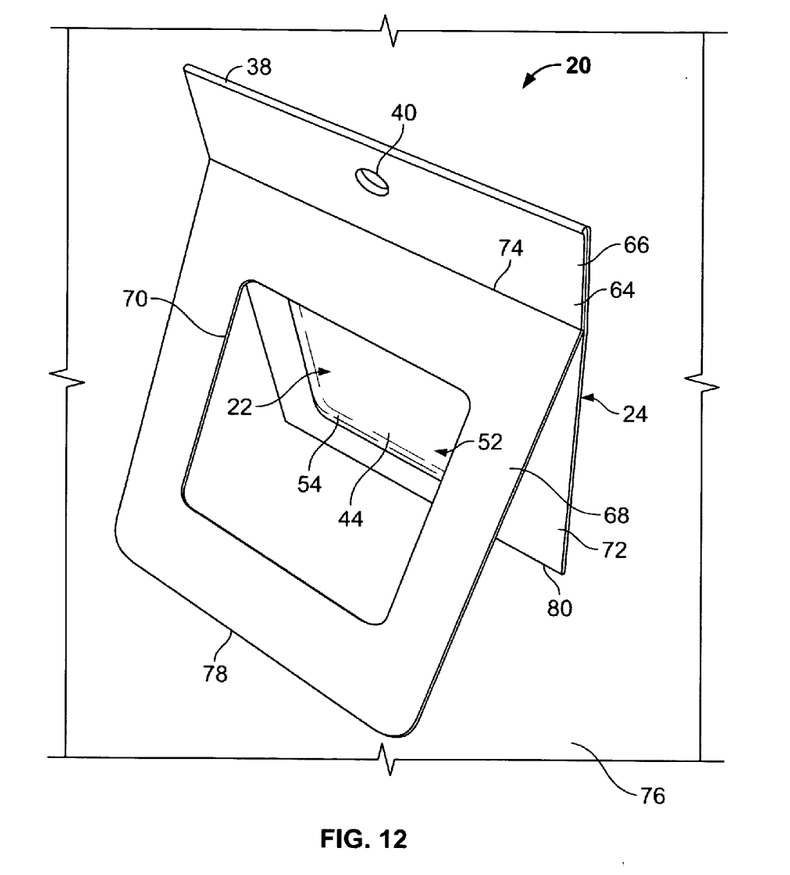
FIG. 12 is a rear isometric view of the dispensing system of FIG. 9.

Referring now to FIGS. 9-12, the dispensing system 20 is disposed in the second state. With particular reference to FIG. 12, the rear face 64 of the display frame 24 is shown. The third wall portion 68 is rotated about a hinge 74 to extend outwardly from the remaining portions of the display frame 24. In the second state, the cup-shaped structure 52 does not extend through the second opening 70 and is no longer aligned therewith. The third wall portion 68 acts as a support member or foot member to assist in propping up the dispensing system 20 from a support surface 76. FIG. 11 illustrates that the dispensing system 20 takes on a substantially inverted V-shape in the second state with the second wall portion 66 and portions of the first wall portion 28 extending therefrom at an angle. A bottom end 78 of the third wall portion 68 and a bottom end 80 of the combined first and fourth wall portions 28, 72 exert forces upon the support surface 76 to maintain the dispensing system 20 in an upright position in the second state.

The third wall portion 68 is actuable between the first state and a plurality of positions that define the second state. Prior to placing the dispensing system 20 in the second state, the third wall portion 68 is juxtaposed with the fourth wall portion 72 and substantially parallel therewith in a first position. The dispensing system is placed in the second state by rotating the third wall portion 68 about the hinge 74. Rotation of the third wall portion 68 causes same to be angled from the fourth wall portion 72 and placed in a second position. The third wall portion 68 may be angled anywhere between about 1 degree to about 180 degrees to place the dispensing system 20 in the second state. Illustratively, the angle of the third wall portion 68 is between about 20 degrees and about 70 degrees.

Regardless of whether the dispensing system 20 is in the first or second state, the permeable membrane 50 of the dispenser 22 is directed substantially away from the rear face 64 of the display frame 24. The volatile material 58 is therefore emitted into the atmosphere without obstruction, thereby allowing for more efficient diffusion of the volatile material 58. The permeable membrane 50 is also viewable from the front face 26 of the dispensing system 20. A user may therefore determine the level of the volatile material 58 remaining in the dispenser 22 without exercising great effort.

Figure 13:
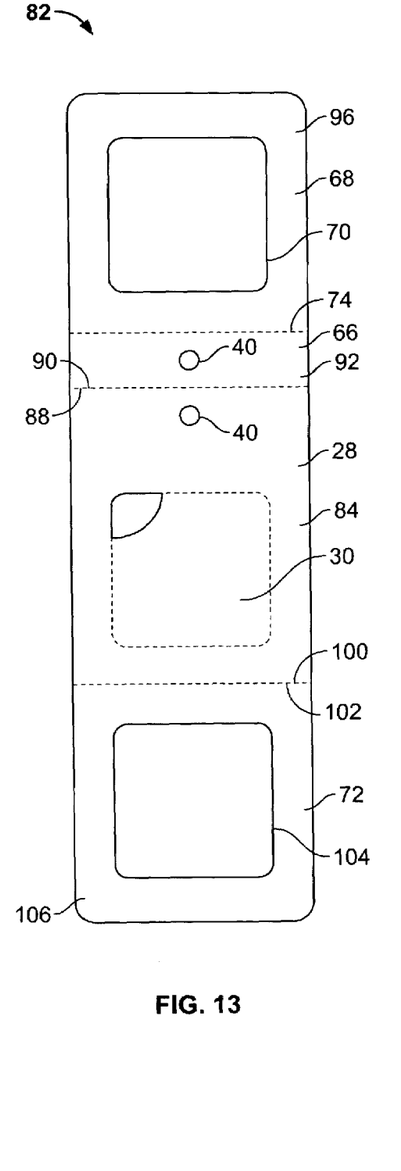
FIG. 13 is a plan view of a front side of a blank used to manufacture the dispensing system of FIGS. 1 and 6-12.
Figure 14:
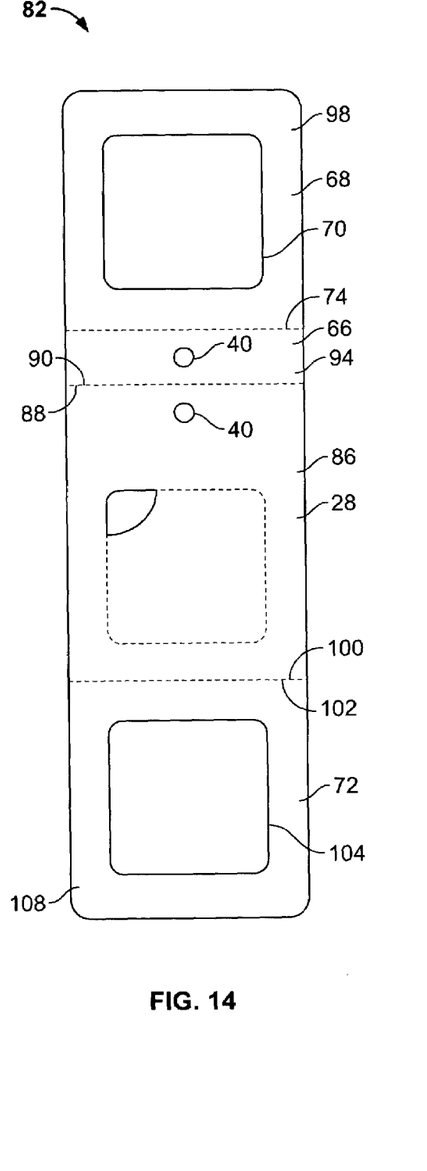
FIG. 14 is a plan view of a rear side of the blank of FIG. 13.

FIGS. 13 and 14 illustrate one type of blank 82 that may be used to manufacture the present dispensing system 20. The blank 82 may be manufactured from paperboard or the like and die cut into the appropriate shape. FIG. 13 depicts a front side 84 of the first wall portion 28 with the removable cover 30 and the hole 40. FIG. 14 depicts a rear side 86 of the first wall portion 28. The second wall portion 66 is attached to a first end 88 of the first wall portion 28 by a hinge 90 or a fold line. The second wall portion 66 also includes the hole 40 and front and rear sides 92, 94, respectively. The third wall portion 68 is attached to the opposite end of the second wall portion 66 at the hinge 74 or a fold line. The third wall portion 68 includes the second opening 70 and front and rear sides 96, 98, respectively. The fourth wall portion 72 is attached to a second end 100 of the first wall portion 28 by a hinge 102 or a fold line. The fourth wall portion 72 includes a third opening 104 similar in dimensions to the second opening 70 and front and rear sides 106, 108, respectively.

The dispensing system 20 is assembled by inserting the cup shaped structure 52 of the dispenser 22, which is not shown in FIG. 13, through the third opening 104 from the rear side 108 of the fourth wall portion 72. The peripheral flange 46 of the dispenser 22 is hot sealed onto portions of the rear side 108 of the fourth wall portion 72 surrounding the third opening 104. The fourth wall portion 72 is rotated about the hinge 102 to position the rear side 108 of the fourth wall portion 72 substantially flush with the rear side 86 of the first wall portion 28. The rear side 108 of the fourth wall portion 72 and the rear side 86 of the first wall portion 28 are hot sealed together. When the fourth wall portion 72 is positioned in such a manner the impermeable laminate 48 of the dispenser 22 is centered behind the cover 30 of the first wall portion 28. The second wall portion 66 is folded about the hinge 90 so that the holes 40 are aligned. The rear side 94 of the second wall portion 66 is similarly hot sealed to the rear side 86 of the of the first wall portion 28. The remaining third wall portion 68 lies substantially flush against the fourth wall portion 72 so that the rear side 98 of the third wall portion 68 is juxtaposed against the front side 106 of the fourth wall portion 72.

Figure 15:
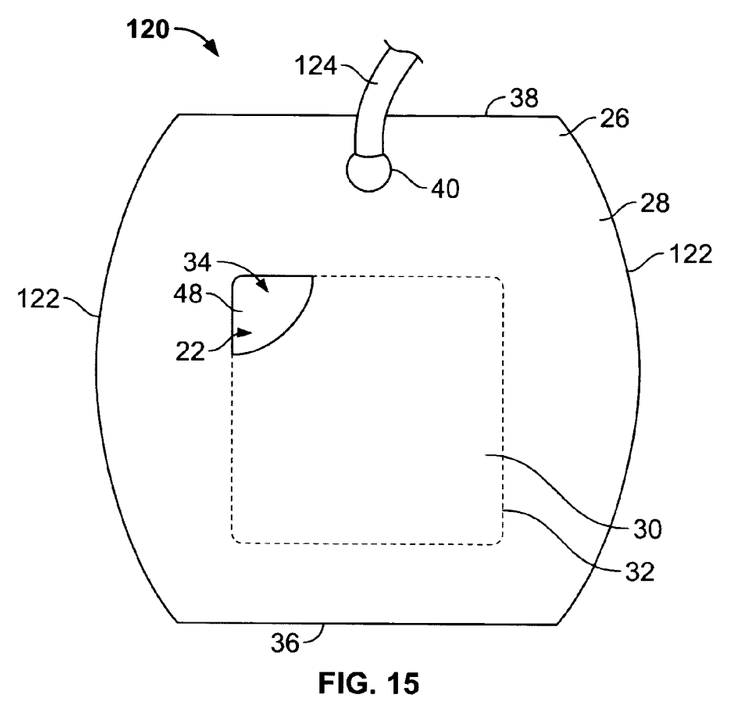
FIG. 15 is a front elevational view of a second dispensing system in a first state that includes a frame and a dispenser.
Figure 16:
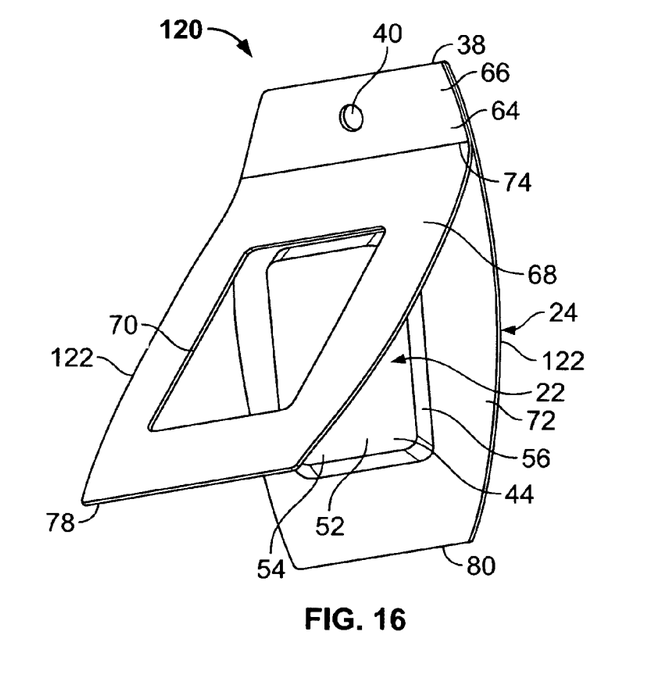
FIG. 16 is a rear isometric view of the second dispensing system of FIG. 15 in a second state.

The blank 82 may comprise any other type of paper based material or a different material such as plastic. Different materials such as plastics may be useful in humid environments that would otherwise be harmful to paper based materials. Further, portions of the blank 82 and the dispenser 22 may be adhered to one another by an adhesive or different type of glue. The display frame 24 itself may also be shaped in a decorative manner for aesthetic effect or provided with varying colors and/or pictures. FIGS. 15 and 16 depict one such dispensing system 120, wherein like reference numerals are assigned with respect to similar structure utilized in the dispensing system 20. The dispensing system 120 is characterized by curved side walls 122 of the first, second, third, and fourth wall portions 28, 66, 68, 72. The dispensing system 120 is also provided with a string 124 that is threaded through the hole 40. The string 124 may be used to support the dispensing system 120 from a support surface such as a rod or door knob. The present embodiment may also be provided without the cover 30 to omit material that has to be discarded. FIGS. 15 and 16 are illustrative of the variations that may be found in other embodiments with respect to the size and shape of various wall portions.

Figure 17:
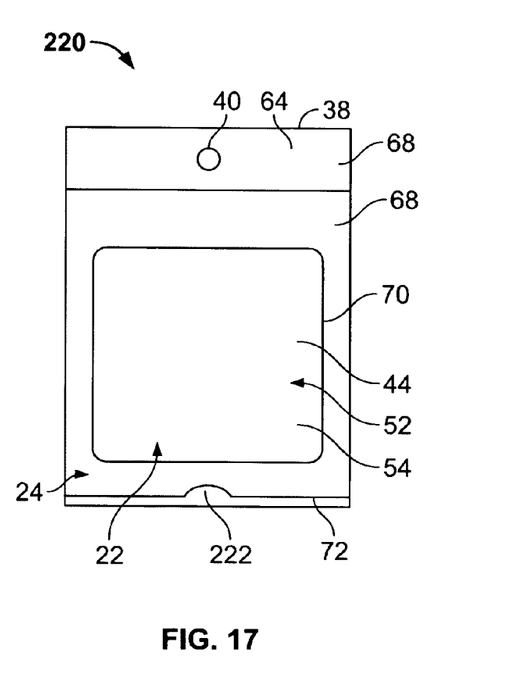
FIG. 17 is a rear elevational view of a third dispensing system in a first state that includes a frame and a dispenser.
Figure 18:
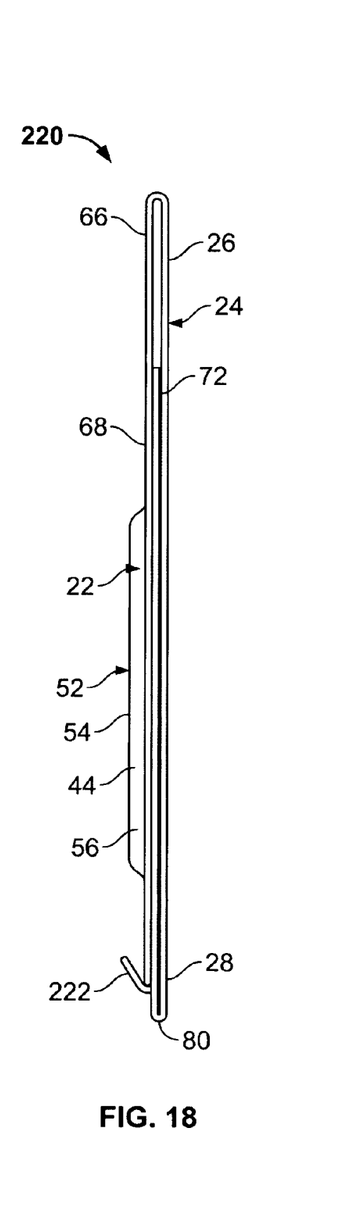
FIG. 18 is a side elevational view of the third dispensing system of FIG. 17.

FIGS. 17 and 18 depict a different embodiment of a dispensing system 220 similar to the dispensing system 20. However, the dispensing system 220 differs in that a retention member 222 is provided on the fourth wall portion 72 adjacent the bottom end 80 of the combined first and fourth wall portions 28, 72. The retention member 222 comprises a resilient curved member that is partially cut away from the fourth wall portion 72 and that is angled outwardly toward the third wall portion 68. When the dispensing system 220 is in the first state, a portion of the bottom end 78 of the third wall portion 68 is retained within the retention member 222. Retention of the third wall portion 68 within the retention member 222 causes the bottom end 78 of the third wall portion 68 to be held against the fourth wall portion 72. Removal of the third wall portion 68 from the retention member 222 transitions the dispensing system 220 from the first state to the second state. The retention member 222 provides the dispensing system 220 with enhanced means for maintaining the dispensing system 220 in the first state. For example, the retention member 222 may prevent an inadvertent state transition from an outside force acting on the dispensing system 220 or from movement of the third wall portion 68 due to over-flexing of the hinge 74. It is envisioned that other types of retention members may be used that are of varying shape, number, or placement. Further, a retention member may be integral with the display frame as shown with respect to FIGS. 17 and 18 or may be a separate structure attached to the display frame.

In a different embodiment, the dispensing systems 20, 120, 220 are provided with openings and dispensers of varying shapes. For example, the dispenser 22 may be fashioned in the shape of a rectangle or other design, such as a snowflake or an animal. Further, multiple dispensers may be provided in a single dispensing system 20, 120, 220 with different or similar volatiles disposed therein. It is also envisioned that a re-usable adhesive may be used to hold some or all of the first, second, third, and fourth wall portions 28, 66, 68, 72 and the dispenser 22 together so that the dispenser 22 may be replaced as opposed to replacing the entire dispensing system 20, 120, 220 after the volatile material 58 has expired. In yet another embodiment, the dispensing systems 20, 120, 220 may be placed on a side thereof so that the bottom and top ends 36, 38 of the dispensing systems 20, 120, 220 do not touch a support surface. Rather, portions of the first, second, third, and fourth wall portions 28, 66, 68, 72 defining either a left or right side of the dispensing system 20, 120, 220 are disposed adjacent the support surface. The third wall portion 68 is still rotated about the hinge 74 to transition between first and second states and offers a user a different way of operating the present dispensing systems 20, 120, 220 as disclosed herein. Those skilled in the art will appreciate the numerous variations that may be made with respect to the present disclosure and which is intended to be captured by the present disclosure.

INDUSTRIAL APPLICABILITY

The air freshener dispensing system described herein advantageously combines the functional and aesthetic characteristics of a display frame that is adjustable between a hanging position and a stand alone position with a fragrance dispenser. Thus, the use of the air freshener dispensing system provides a user greater flexibility in positioning an air freshener within a home or office setting.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What is claimed is:

1. A device adapted to discharge a volatile material, comprising:
   a display frame having a front face and a rear face;
   an opening disposed in the front face; and
   a dispenser disposed within the display frame, wherein the dispenser comprises a blister holding a volatile material, a permeable membrane extending across an open end of the blister,
   wherein the rear face includes an integral foot member actuable between first and second states,
   wherein the permeable membrane is disposed adjacent the front face and prevents the release of the volatile material in a first condition and permits the release of the volatile material through the opening in a second condition, and
   wherein an impermeable laminate is disposed substantially over the entirety of the permeable membrane in the first condition.

2. The device of claim 1, wherein a removable cover overlies the opening disposed in the front face.

3. The device of claim 1, wherein removal of the impermeable laminate causes the device to enter the second condition.

4. The device of claim 1, wherein actuation of the integral foot member between the first and second states does not interrupt the release of the volatile material from the dispenser.

5. The device of claim 1, wherein the device is in the first state when the integral foot member is substantially parallel with the front face.

6. The device of claim 1, wherein a retention member holds the integral foot member in the first state.

7. The device of claim 1, wherein the device is in the second state when the integral foot member is substantially angled from the front face.

8. The device of claim 1, wherein the integral foot member is rotatable between first and second positions.

9. The device of claim 8, wherein the integral foot member is substantially parallel with the front face in the first position.

10. The device of claim 8, wherein the integral foot member is angled from about 1 degree to about 180 degrees from the front face in the second position.

11. The device of claim 1 further comprising a hole extending from the front face to the rear face adjacent a top end of the display frame.

12. A substantially flat blank adapted for assembly into a dispensing system, the blank comprising:
   a first wall portion with a removable cover extending across a first opening;
   a second wall portion hingedly connected to a first end of the first wall portion about a first fold line;
   a third wall portion hingedly connected to an end of the second wall portion about a second fold line, the third wall portion further including a second opening; and
   a fourth wall portion hingedly connected to a second end of the first wall portion about a third fold line, the fourth wall portion further including a third opening adapted to receive a reservoir of a volatile material holding dispenser,
   wherein the second and third openings are substantially the same size and are adapted to align within one another during a first in use position.

13. The blank of claim 12, wherein a reservoir of a volatile material holding dispenser is inserted through the third opening from a rear side of the fourth wall portion during assembly of the dispensing system.

14. The blank of claim 13, wherein the dispenser is affixed onto the rear side of the fourth wall portion.

15. The blank of claim 13, wherein the fourth wall portion is rotated about the third fold line to position the rear side of the fourth wall portion substantially parallel with a rear side of the first wall portion.

16. The blank of claim 15, wherein the rear side of the fourth wall portion is affixed to the rear side of the first wall portion and the dispenser is aligned with the cover.

17. The blank of claim 12, wherein the second wall portion is rotated about the first fold line to position a rear side thereof substantially parallel to a rear side of the first wall portion, and wherein the first and the second wall portions are affixed to one another.

18. The blank of claim 17, wherein the third wall portion is rotatable between a first position and a second position.

19. A method of operating a volatile material dispenser, comprising:
   providing an inverted V-shaped structure having first and second sides, wherein the first side retains a volatile material dispensing cartridge and the second side includes a support member actuable between first and second positions;
activating the volatile material dispensing cartridge; and
disposing the support member in at least one of the first and second positions,
wherein the first position is characterized by the support member being substantially flush with the first side,
wherein the second position is characterized by the support member being angled from the first side a distance sufficient to support the V-shaped structure, and
wherein actuation of the support member between the first and second positions does not interrupt the release of volatile material from the cartridge.

* * * * *